United States Patent
Chisholm et al.

(10) Patent No.: US 10,155,066 B2
(45) Date of Patent: Dec. 18, 2018

(54) HARDENABLE MULTI-PART ACRYLIC COMPOSITION

(71) Applicant: Lucite Int'l Specialty Polymers & Resins Ltd., Southampton Hampshire (GB)

(72) Inventors: Michael Stephen Chisholm, Newton Aycliffe (GB); Sera Saheb Abed-Ali, Newton Aycliffe (GB)

(73) Assignee: LUCITE INTERNATIONAL SPECIALTY POLYMERS & RESINS LIMITED, Southampton Hampshire (GB)

(*) Notice: Subject to any disclaimer, the term of this patent is extended or adjusted under 35 U.S.C. 154(b) by 169 days.

(21) Appl. No.: 15/025,747

(22) PCT Filed: Sep. 30, 2014

(86) PCT No.: PCT/GB2014/052949
§ 371 (c)(1),
(2) Date: Mar. 29, 2016

(87) PCT Pub. No.: WO2015/044688
PCT Pub. Date: Apr. 2, 2015

(65) Prior Publication Data
US 2016/0279289 A1    Sep. 29, 2016

(30) Foreign Application Priority Data

Sep. 30, 2013  (GB) .................................. 1317302.6
Mar. 26, 2014  (GB) .................................. 1405394.6

(51) Int. Cl.
*A61L 27/16*    (2006.01)
*A61L 27/50*    (2006.01)
(Continued)

(52) U.S. Cl.
CPC ............ *A61L 27/16* (2013.01); *A61K 6/0079* (2013.01); *A61K 6/083* (2013.01); *A61L 24/001* (2013.01);
(Continued)

(58) Field of Classification Search
None
See application file for complete search history.

(56) References Cited

U.S. PATENT DOCUMENTS 3,882,858 A * 5/1975 Klemm ................ A61K 9/0024
                                                606/76
4,141,864 A * 2/1979 Rijke ..................... A61K 6/033
                                                433/173
(Continued)

FOREIGN PATENT DOCUMENTS

EP    0218471 A1    4/1987
JP    H0678987 A    3/1994
(Continued)

OTHER PUBLICATIONS

OR Handbook for Simplex P Bone Cement, Stryker Orthopaedics, 2007.*
(Continued)

*Primary Examiner* — Peter A Salamon
(74) *Attorney, Agent, or Firm* — Shumaker, Loop & Kendrick, LLP

(57) ABSTRACT

A hardenable multi-part acrylic composition comprises a solid first part and a storage stable liquid second part and optionally, further solid and/or liquid parts, the parts being operable to form a cement which hardens to a solid mass upon mixing. The composition further comprises an acrylic monomer component in the second part, an initiator component, a first sub-population of acrylic polymer particles in the first and/or further parts, a second sub-population of
(Continued)

SEM image of the spray dried powder of preparative example 1(3 micron scale bar)

acrylic polymer particles in the first and/or further parts and optionally, one or more further sub-population(s) of acrylic polymer particles, and a radiopacifying filler. The initiator component amount is effective to polymerize the acrylic monomer component upon mixing. At least some of the radiopacifying filler is encapsulated within and/or adsorbed on the first sub-population of acrylic polymer particles and the second sub-population of acrylic polymer particles has a lower average particle size than the first.

32 Claims, 1 Drawing Sheet

(51) Int. Cl.
| | |
|---|---|
| *A61L 24/06* | (2006.01) |
| *A61L 24/00* | (2006.01) |
| *C08F 265/06* | (2006.01) |
| *C09J 4/06* | (2006.01) |
| *C09J 133/12* | (2006.01) |
| *A61K 6/00* | (2006.01) |
| *A61K 6/083* | (2006.01) |

(52) U.S. Cl.
CPC .............. *A61L 24/06* (2013.01); *A61L 27/50* (2013.01); *C08F 265/06* (2013.01); *C09J 4/06* (2013.01); *C09J 133/12* (2013.01)

(56) References Cited

U.S. PATENT DOCUMENTS

| | | | | |
|---|---|---|---|---|
| 4,404,327 A * | 9/1983 | Crugnola | ................ | A61L 24/06 523/115 |
| 4,500,658 A | 2/1985 | Fox | | |
| 4,791,150 A * | 12/1988 | Braden | ............... | A61L 24/0089 523/116 |
| 4,837,279 A * | 6/1989 | Arroyo | ................. | A61L 24/043 523/116 |
| 4,963,151 A * | 10/1990 | Ducheyne | .......... | A61B 17/8802 428/297.4 |
| 5,276,070 A * | 1/1994 | Arroyo | ................... | A61L 24/06 523/116 |
| 5,334,626 A | 8/1994 | Lin | | |
| 5,795,922 A * | 8/1998 | Demian | ................ | A61L 24/001 424/419 |
| 7,259,210 B2 * | 8/2007 | Puckett, Jr. | ............. | A61L 24/06 523/115 |
| 2004/0132859 A1 * | 7/2004 | Puckett, Jr. | ............. | A61L 24/06 523/118 |
| 2012/0035296 A1 | 2/2012 | Nakamura et al. | | |
| 2012/0195848 A1 * | 8/2012 | Lu | ....................... | A61L 24/0089 424/78.31 |

FOREIGN PATENT DOCUMENTS

| | | |
|---|---|---|
| JP | 2009221171 A | 10/2009 |
| RU | 2195320 C2 | 12/2002 |
| WO | 2009/108893 A2 | 9/2009 |
| WO | 2010/018412 A1 | 2/2010 |
| WO | 2010098305 A1 | 9/2010 |

OTHER PUBLICATIONS

International Search Report for PCT/GB2014/052949 dated Jan. 29, 2015 (6 pages).

Office Action for Russian Patent Appln. No. 2016116769(026344), dated Jul. 11, 2018 (10 pages including English translation).

* cited by examiner

Figure 1: SEM image of the spray dried powder of preparative example 1 (3 micron scale bar)
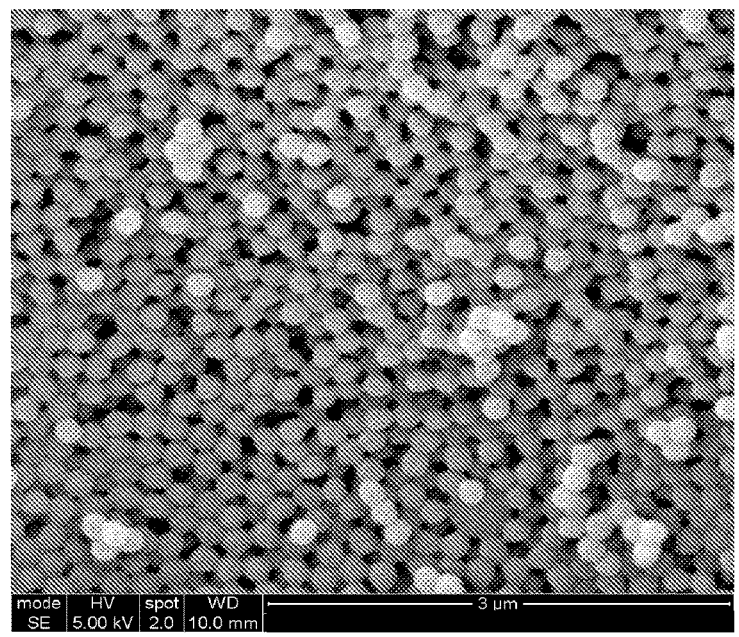
Figure 2: SEM image of Colacryl® B866 PMMA bead polymer (3 micron scale bar)
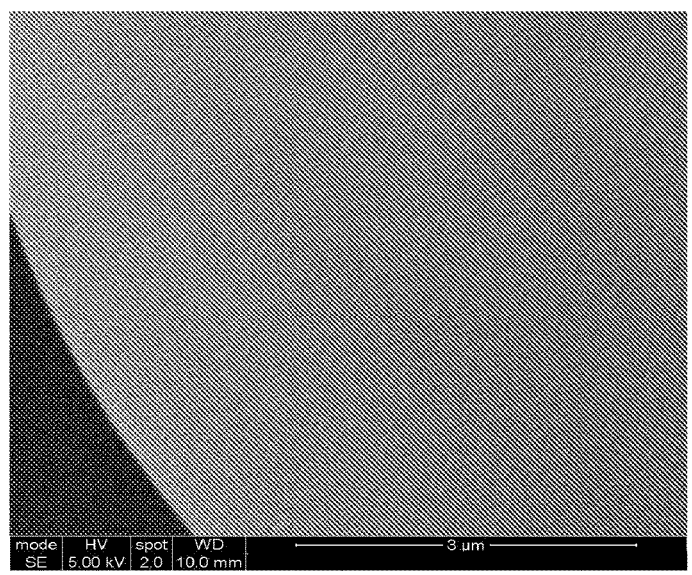

HARDENABLE MULTI-PART ACRYLIC COMPOSITION

CROSS-REFERENCE TO RELATED APPLICATION

This U.S. National Stage Application claims priority from PCT/GB2014/052949 filed Sep. 30, 2014, which claims priority from GB 1405394.6 filed Mar. 26, 2014 and GB 1317302.6 filed Sep. 30, 2013, the entirety of which are incorporated herein by reference.

TECHNICAL FIELD AND BACKGROUND OF THE INVENTION

The present invention relates to a hardenable multi-part polymer composition comprising a radiopacifying filler, in particular but not exclusively, an acrylic composition which has at least two parts which react with each other upon being mixed together to form a cement such as a bone cement which hardens to a solid.

Hardenable compositions formed by mixing together acrylic polymers and monomers are useful in a wide range of applications. Particular utility is found in dental, medical, adhesive and construction applications, where such materials have been used for over 40 years.

Dental applications include denture bases, denture base plates, denture liners, denture repairs, custom trays, veneering for crowns and bridgework, artificial teeth, veneers and repair for natural teeth and tooth restorative fillings. Medical applications include bone cements for bone cavities such as prosthetic cements, cranial cements and vertebral cements in vertebroplasty and kyphoplasty. Further applications include the production of shaped articles that harden extra-corporeally and which can then be introduced into the body.

One type of hardenable acrylic compositions in which the invention is advantageous is generally composed of a solid component and liquid component. The solid component comprises a powder formed from polymer particles and, if appropriate, further additives, such as polymerisation initiators and catalysts, fillers and dyestuffs. The liquid component comprises a liquid monomer or monomers and further additives, such as accelerators and stabilisers. When ready for use, the solid and liquid components are mixed together to form a liquid or semi-solid paste, which, under the action of the polymerisation initiators and accelerators, increases in viscosity and hardens into a solid.

The solid component typically used consists of small spherical beads (usually about 20-150 microns in diameter) of poly(methyl methacrylate) (PMMA) and a small amount of polymerisation initiator such as dibenzoyl peroxide (BPO), usually encapsulated within the PMMA bead, but which can also be added as a separate component. The liquid component is usually a monomer, typically methyl methacrylate (MMA), which may also contain a polymerisation activator such as N, N-dimethyl-p-toluidine (a tertiary amine) (DMPT) and an inhibitor such as hydroquinone (HQ) to prevent the monomer from spontaneously polymerising.

When the solid and liquid components are mixed together, the polymer particles are wetted with monomer, solvated and begin to dissolve. The solvated polymer particles release dibenzoyl peroxide initiator into the monomer which interacts with activator, if present, to produce radicals that react with the monomer and initiate room temperature addition polymerisation of the monomer. The mixture starts out at a relatively low viscosity and progresses to a stiffer and stiffer system that eventually hardens completely.

Compositions hardenable at room temperature (so-called "self-curing" or "cold-curing" systems) have dough times that are typically 4 to 10 minutes and set times that are typically 10 to 25 minutes in duration. The work time effectively defines the time period available for the operator to manipulate the dough in the desired fashion, for example pressing into a denture mould for denture base manufacture, or pressing into a bone cavity during hip repair or replacement or injecting into a vertebral cavity during spinal surgery or forcing into a gap or cavity during industrial cementing operations. The dough time is determined by the rate at which the combination of solid and liquid components rise in viscosity immediately after mixing and is controlled by a number of factors, such as polymer bead particle size and shape, polymer molecular weight, and polymer composition.

Radiopacifying fillers such as barium sulphate or zirconium dioxide are a necessary ingredient to add to bone cement compositions. They function as X-ray contrast agents to show the location of bone cements when implanted in the body. Radiopacifying fillers may traditionally be added to a solid-liquid bone cement composition in either the solid component or liquid component, or both. However, the introduction of filler particles has a tendency to reduce the mechanical properties of the hardened composition such as flexural, tensile and fatigue properties.

U.S. Pat. No. 4,500,658 discloses that a problem with certain types of metal filler such as lead foil, silver alloy, gold and 1% set amalgam are that they cause stress concentrations at the interface between the insert and the resin which weakens and fractures the material.

On the other hand, heavy metal compounds externally attached to the beads are inconvenient. In addition, it is pointed out that high levels of barium sulphate are necessary in the resin to render it radiopaque but that at these levels there is a negative impact on the strength of the material. The document describes that the filler can be encapsulated and uniformly dispersed in the bead using suspension polymerisation. The beads are said to be useful in biomedical applications to colour biomedical materials and devices. An example is proposed of compounding the bead particles into a dry powder for a solid-liquid denture composition. The beads may be ground up prior to use in a composition. The mixtures with monomer disclosed imply that most of the bead is dissolved in the monomer thereby allowing encapsulated radiopaque pigment to disperse in the monomer. Accordingly, the document merely teaches a manner of opacifier delivery to the matrix of the final polymer.

EP0218471 teaches that barium sulphate radiopacifier incorporated into ethyl methacrylate polymer beads can give improved mechanical properties with n-butyl methacrylate monomer in a solid-liquid system. There is no mention of the possibility to reduce the concentration of radiopacifying filler particles through encapsulating within acrylic polymer bead particles. Furthermore, upon mixing the bead polymer is said to be almost fully dissolved in monomer so that there is no intention to maintain encapsulation of radiopacifying filler in the final product. It is one object of the present invention to provide bone cements and dental compositions with improved mechanical properties.

SUMMARY OF THE INVENTION

Surprisingly, a hardenable solid-liquid multi-part composition and methods of production thereof have been discovered that introduce radiopacifying filler without significantly affecting mechanical properties in the hardened composition. Advantageously, therefore, compositions are provided with improved mechanical properties such as improved flexural, tensile and fatigue properties.

DETAILED DESCRIPTION

According to a first aspect of the present invention there is provided a hardenable multi-part acrylic composition comprising a solid first part and a storage stable liquid second part and optionally, further solid and/or liquid parts, the parts being operable to form a cement which hardens to a solid mass upon mixing of the parts together, the composition further comprising an acrylic monomer component in the second part, an initiator component, a first sub-population of acrylic polymer particles in the first and/or further parts, a second sub-population of acrylic polymer particles in the first and/or further parts and optionally, one or more further sub-population(s) of acrylic polymer particles, and a radiopacifying filler, the initiator component being present in an amount effective to polymerize the acrylic monomer component upon being mixed and/or activated therewith characterized in that at least some of the radiopacifying filler is encapsulated within and/or adsorbed on the first sub-population of acrylic polymer particles and wherein the second sub-population of acrylic polymer particles has a lower average particle size than the first sub-population.

Typically, the first sub-population and/or the second sub-population are in the first part. The first and/or second sub-population may also be in a third or further part. However, preferably, at least one of the first or second sub-populations and more preferably both sub-populations are in the first part. As indicated, the composition may include more than two parts, for instance the initiator component and/or any of the sub-populations could be stored in a separate third part but for convenience the multi-part acrylic composition of any of the aspects of the invention herein is typically only a two-part composition, i.e. there is no third or further part.

The acrylic polymer composition comprises two or more sub-population(s) of acrylic polymer particles. A sub-population may be generally distinguishable from the other sub-population(s) by one or more properties such as molecular weight (MW), molecular weight distribution, porosity, the nature and distribution of the (co)monomer residues, particle size, particle size distribution, and/or type, the presence or absence of residual initiator and, if present, the amount and type of residual initiator. The two or more sub-populations of acrylic polymer particles may therefore be of one or more types for example suspension polymerized, emulsion polymerized, solution polymerized and/or bulk polymerized. Typically, if suspension, bulk or solution polymerized the sub-population(s) are present as polymer beads and if emulsion polymerized the sub-population(s) are present as emulsion polymerized microparticles which may be coalesced together, agglomerated together or independent. Alternatively, the sub-population(s) may be present as crushed, milled, or ground bulk polymerized acrylic polymer or crushed, milled, or ground acrylic polymer beads.

The acrylic composition solid first part and storage stable liquid second part are preferably stored and reacted between 0 and 30° C., more preferably, between 18 to 25° C., most preferably, between 20 to 23° C. and in any case typically under normal atmospheric pressure ranges. The preparation of a cement from the mixing of the acrylic composition solid first part and the liquid second part can be carried out in various ways that will be appreciated by those skilled in the art, for example by hand mixing.

Typically, the initiator component is present in an amount effective to fully polymerize the monomer component. For example, to at least polymerize 85% w/w of the monomer component, more typically, at least 90% w/w, most typically, 95%-98% w/w of the monomer component. In addition, the initiator component may be present in excess of the amount that would be effective to fully polymerize the monomer component.

Typically, at least 25% w/w of the total radiopacifying filler present in the composition and therefore, typically, also in the final hardened composition, is encapsulated within and/or adsorbed on acrylic polymer particles, more typically, at least 50% w/w, most typically, at least 75% w/w is so encapsulated and/or adsorbed.

Therefore, between 20 and 100% w/w of the radiopacifying filler in the composition and therefore, typically, also in the final hardened composition, is encapsulated within and/or adsorbed on acrylic polymer particles, more typically, between 30% and 100% w/w, most typically, between 60 and 100% w/w. Although it is preferred for the level of encapsulated and/or adsorbed radiopacifying filler to be maintained in the final hardened composition there may nevertheless be some dissolution of the carrier particle in the monomer and accordingly, in the alternative, the level of the radiopacifying filler in the final hardened composition which is encapsulated within and/or adsorbed on acrylic polymer particles is between 10 and 100% w/w, more typically, between 20% and 95% w/w, most typically, between 50 and 90% w/w.

Typically, the level of radiopacifying filler in the hardenable multi-part composition of the invention is between 1 and 50% w/w, more typically, between 5 and 40% w/w most typically, between 6.5 and 30% w/w. Preferably, the radiopacifying filler is present at the composition levels specified encapsulated within or adsorbed on the acrylic polymer particles. Typically, the radiopacifying filler is present at or around the compositional levels specified encapsulated within or adsorbed on the acrylic polymer particles in the hardened cement i.e. the fully polymerized product. Accordingly, the encapsulated and or adsorbed radiopacifying filler should preferably not be released into the matrix monomer and is therefore typically present at the composition levels specified in or on acrylic polymer particles. However, during mixing some of the adsorbed radiopacifying filler may migrate into the monomer and, in addition, some of the polymer particles may dissolve thus releasing radiopacifying filler into the matrix monomer. Accordingly, the level of encapsulated radiopacifying filler present in the final hardened cement may be reduced in the compositional levels above by up to 40%, more typically, by up to 20%.

Advantageously, a high level of encapsulation in the final hardened product is achieved by incorporating at least a second sub-population(s) of acrylic polymer particles into the composition having a lower average particle size than the average particle size of the first sub-population of acrylic polymer particles having encapsulated and/or adsorbed radiopacifying filler. The average particle size of this second sub-population is typically <30 µm, more typically <20 µm, most typically <10 µm. Typical lower average particle size second sub-population ranges being 0.01-30 µm, more typically, 0.02-20 µm, most typically, 0.1-10 µm. Such lower average particle size sub-populations may be present in any of the parts of the hardenable composition but are generally kept apart from the monomer so that they preferentially dissolve in the monomer after mixing to prevent or reduce dissolution of the first sub-population having encapsulated and/or adsorbed radiopacifying filler. Accordingly, the larger average particle size acrylic polymer particle first sub-population with encapsulated and/or adsorbed radiopacifying filler does not dissolve or does not dissolve to the same extent in the monomer as the lower average particle size second sub-population. The further sub-populations may have larger or lower average particle sizes than the first sub-population and/or have encapsulated and/or adsorbed radiopacifying filler. However, it is preferred that at least a second sub-population has a lower average particle size than all sub-populations with encapsulated and/or adsorbed radiopacifying filler present in the composition and it is also independently preferred that the second sub-population is essentially free of encapsulated radiopacifying filler wherein by free is meant less than 5% w/w, more typically, less than 1% w/w radiopacifying filler.

Accordingly, when emulsion polymerized microparticles, the Z-average particle size of the lower average particle size sub-population(s) whether the second or further sub-population(s) is preferably in the range 0.01 to 2 µm, more preferably, 0.02 to 1 µm, most preferably, 0.05 to 0.5 µm, especially, 0.1 to 0.45 µm.

When bead particles, the mean particle size of the lower average particle size sub-population(s) whether the second or further sub-population(s), is preferably, in the range 1-30 µm, more preferably, 2-20 µm, most preferably, 2.5-15 µm.

Although any acrylic polymer particle may be used as the lower average particle size sub-population(s), it is preferred that emulsion polymerized microparticles as defined herein are used.

The average particle size of the sub-population(s) having encapsulated and/or adsorbed radiopacifying filler is preferably in the range 10 to 1000 µm, more preferably, 20 to 600 µm, most preferably, 25 to 200 µm. Generally, in such a range this should be taken to refer to mean particle size.

Generally, herein the average particle size is determined by a technique appropriate to the size of the particle being characterised. Accordingly, a lower average particle size sub-population may have its average particle size characterised by a different technique than the sub-population it is being compared with. Nevertheless, this is appropriate where the average particle sizes of the relevant sub-populations are clearly distinguishable. Where the average particle size is relatively close it may be appropriate to use only the same technique. For instance, sub-micron particles may be characterised by their Z-average particle size whereas particles > 10 µm can be characterised by their mean particle size. Particles between 1 and 10 µm could be characterised by either measurement and if both sub-populations for comparison fall in this range then the same technique should be adopted. Accordingly, herein, emulsion polymerized microparticles are preferably characterised by their Z-average particle size and bead particles are preferably characterised by their mean particle size.

Preferably, the lower average particle size sub-population particle size whether the second or further sub-population(s) is sufficiently lower than the sub-population having encapsulated and/or adsorbed radiopacifying filler particle size to retard dissolution of the latter in monomer. Preferably, the average particle size whether the second or further sub-population(s) is at least 10% lower than the average particle size of the larger particle.

Notwithstanding the above, it is also possible for some radiopacifying filler to be present in the composition and/or hardened cement in a form that is not encapsulated and/or adsorbed in or on acrylic polymer particles, for example in the acrylic composition first part and/or liquid second part. This is either independently added radiopacifying filler or radiopacifying filler that has migrated from an encapsulated or adsorbed form into the surrounding liquid.

The encapsulated and/or adsorbed radiopacifying filler may be encapsulated within and/or adsorbed on only the first sub-population or in more than one sub-population of acrylic polymer particles. If the sub-populations extend to more than one type (such as bead and emulsion) of acrylic polymer particle, the radiopacifying filler may be present in any one or more types. Preferably, however, the radiopacifier is encapsulated within and/or adsorbed on one or more polymer bead sub-populations. Therefore, the first sub-population is preferably acrylic bead polymer particles.

Preferably, at least 90% w/w of the total acrylic monomer component in the composition is present in the liquid second part, more preferably, at least 95% w/w, most preferably, at least 99% w/w. In preferred embodiments, substantially all the acrylic monomer component in the composition is present in the liquid second part. Typically, therefore, the acrylic monomer component is present in only one part of the composition. Typically, the acrylic monomer component containing liquid part includes acrylic polymer particles dissolved therein.

Typically, the said acrylic monomer component and the said initiator component are located in separate parts of the said multi-part composition so that the part containing the monomer component is storage stable to polymerization.

The sub-population(s) of acrylic polymer particles whether the first, second or further sub-population(s) may include one or more sub-population(s) of acrylic polymer beads and one or more sub-population(s) of emulsion polymerized microparticles.

Preferably, the radio pacifying filler is encapsulated and/or adsorbed in only the first sub-population of acrylic polymer particles but it may be encapsulated and/or adsorbed in more than one further sub-population as mentioned above. Typically, the radiopacifying filler is only encapsulated within and/or adsorbed on acrylic polymer beads but it may alternatively only, or additionally, be encapsulated in and/or adsorbed on emulsion polymerized microparticles. Typically, it is convenient to have encapsulated and/or adsorbed radiopacifying filler in only one part of the composition, preferably, the first part thereof. If radiopacifying filler is encapsulated and/or adsorbed in only one sub-population type of acrylic polymer particle further sub-population types of acrylic polymer particles may still be present in the composition. For instance, if the radiopacifying filler is encapsulated and/or adsorbed in the emulsion polymerized microparticles or acrylic polymer beads, both types of particles may still be present in the composition. In preferred embodiments, the composition includes acrylic polymer beads in both the first and second parts and typically, emulsion polymerized microparticles in only the first part and optionally radiopacifying filler may be encapsulated and/or adsorbed in any one or more types of acrylic polymer particles in the first part. Preferably, however, the radiopacifying filler is only encapsulated and/or adsorbed in acrylic polymer beads in the acrylic composition first part.

Typically, at least 50% w/w of the total encapsulated and/or adsorbed radiopacifying filler in the composition is present in acrylic polymer beads, more typically, at least 90% w/w, most typically, at least 95% w/w is present in the acrylic polymer beads and more preferably at these levels in the acrylic polymer beads in the acrylic composition first part.

One method of encapsulation is to disperse the radiopacifying filler such as barium sulphate within acrylic monomer, then polymerize the monomer by, for example, bulk, emulsion or suspension polymerization, thereby encapsulating the radiopacifying filler within the resulting acrylic polymer particles.

As indicated, the composition may include emulsion polymerised acrylic particles or bead polymer particles. These may be made in accordance with techniques known to those skilled in the art. However, preferred features of production include:

emulsion polymerizing at least one acrylic monomer composition optionally in the presence of radiopacifying filler to produce an acrylic polymer emulsion optionally with encapsulated and/or adsorbed radiopacifying filler; and/or suspension, bulk or solution polymerizing at least one acrylic monomer composition optionally in the presence of radiopacifying filler to produce an acrylic polymer bead particle optionally with encapsulated and/or adsorbed radiopacifying filler.

The preferred approach is to encapsulate the radiopacifying filler within bead polymer particles such as those produced by suspension polymerization.

It has been surprisingly found that by encapsulating the radiopacifying filler within acrylic polymer particles in a first sub-population in the presence of a lower average particle size second sub-population, the concentration of radiopacifying filler particles in the continuous matrix formed by mixing the acrylic composition first part and liquid second part is reduced, thereby reducing the number of stress concentrating defects in the continuous matrix. As a result, the normal reduction in mechanical properties that would occur if all the filler were to be found in the continuous matrix can be avoided. Further, by initially finely dispersing the radiopacifying filler in monomer and then encapsulating it within the acrylic polymer particle, it is possible to achieve the same radiopacifying effect through use of an even lower amount of filler. This leads to a further enhancement in mechanical properties.

Suitable radiopacifying fillers may be selected from the list comprising zirconium dioxide, strontium carbonate, powdered tantalum, powdered tungsten, barium sulphate and mixtures thereof. Preferably, the radiopacifying filler is barium sulphate. Typically, when the radiopacifying filler is barium sulphate, the barium sulphate is both encapsulated in and adsorbed on the acrylic polymer particles, more typically, bead polymer particles. On the other hand, for other radiopacifying fillers such as zirconium dioxide, the zirconium dioxide is generally only encapsulated.

By radiopacifying herein is meant the ability to render a material more distinguishable from surrounding material when subjected to X-rays.

In a preferred embodiment, the acrylic composition first part comprises an acrylic polymer particle first sub-population present as polymer beads and having encapsulated and/or adsorbed radiopacifying filler. Preferably, the composition of the invention comprises emulsion polymerized microparticles as a second sub-population. Advantageously, the average particle size of emulsion polymerized microparticles is generally lower than the average particle size of polymer beads.

In particularly preferred aspects of the present invention, the acrylic composition solid first part containing a polymer bead first sub-population and having encapsulated and/or adsorbed radiopacifying filler further contains a second sub-population of emulsion polymerized microparticles.

The invention extends in another aspect to a solid cement composition produced from mixing a multi-part acrylic composition according to any of the aspects herein.

Advantageously, the invention is for use in the treatment of human or animal bone.

Furthermore, the invention extends in another aspect to compositions of the acrylic polymer solid first part of the invention for uses as a dough time reduction agent or as a mechanical strength improver in a hardenable multi-part acrylic composition.

According to a further aspect of the present invention there is provided a method of producing an acrylic cement from a multi-part acrylic composition according to any of the aspects of the present invention comprising the step of mixing the said first, second and optionally further parts.

The above mixing process may be by any suitable means, for example a manual mixing process.

According to a further aspect of the present invention there is provided a method of producing a hardenable multi-part acrylic composition according to any of the aspects of the present invention comprising the steps of:

a) producing an acrylic polymer composition first part and a storage stable second part according to the first aspect of the present invention;
   i) wherein step a) comprises the step of polymerizing an acrylic monomer composition to form a sub-population of acrylic polymer particles wherein the polymerization is carried out in the presence of radiopacifying filler to thereby encapsulate the radiopacifying filler in acrylic polymer particles.

According to a second aspect of the present invention there is provided a hardenable multi-part acrylic composition comprising a solid first part and a storage stable liquid second part and optionally, a third or further solid or liquid parts, the parts being operable to form a cement which hardens to a solid mass upon mixing of the parts together, the composition further comprising an acrylic monomer component in the second part, an initiator component, a first sub-population of acrylic polymer beads in the first and/or a further part, and a second sub-population of acrylic emulsion polymerized microparticles in the first and/or a further part, the initiator component being present in an amount effective to polymerize the acrylic monomer component upon being mixed and/or activated therewith characterized in that at least some of the radiopacifying filler is encapsulated within and/or adsorbed on the first sub-population of acrylic polymer beads.

As indicated, the composition includes emulsion polymerized microparticles. These may be made in accordance with techniques known to those skilled in the art. Typically, the emulsion polymerized microparticles are in the form of a network of coalesced emulsion polymerized microparticles, typically produced by drying a liquid emulsion to form a powder.

The different types of acrylic polymer particles may be blended together to form the solid first part of the acrylic composition, typically, in the presence of suitable other composition components known to the skilled person. Such composition additives include initiators, catalysts, dyestuffs and fillers.

Blending the acrylic polymer particles of the invention may be carried out by any suitable technique known to the skilled person for blending different sized particles.

However, the preferred means of blending small and larger particles is through conventional tumble blending methods. Other methods of blending powders are also possible, e.g., screw blending and roll blending.

Advantageously, the multi-part hardenable compositions of the invention also attain a low maximum exotherm temperature during hardening thus avoiding in the case of bone cements, tissue necrosis, a well known problem of acrylic bone cements.

A further advantage is that the hardenable compositions formed from the invention also display a long working time thereby providing a longer time period for the operator to manipulate the cement dough in the desired fashion during application.

The polymerization of at least one acrylic monomer composition to produce an acrylic polymer particle such as the beads or microparticles of the invention may take place with or without excess initiator.

Typically, a preferred embodiment of the hardenable composition of any aspect of the present invention is prepared by:
- a) dispersing the radiopacifying filler in acrylic monomer/polymer syrup to produce a dispersion;
- b) suspension polymerizing the dispersion in the presence of, and optionally, in the presence of excess, initiator to produce acrylic polymer bead particles containing encapsulated and/or adsorbed filler;
- c) emulsion polymerizing an acrylic monomer composition in the presence of, and optionally, in the presence of excess, initiator to produce a polymer emulsion;
- d) drying the polymer emulsion of step c) to produce a network of coalesced emulsion polymerized microparticles;
- e) mixing the acrylic polymer bead particles containing encapsulated and/or adsorbed filler of step b) with the coalesced emulsion polymerized microparticles of step d), optionally, with added initiator, to form the acrylic polymer composition first part;
- f) producing a liquid second part containing acrylic monomer and accelerator;
- g) mixing the acrylic composition first part with the liquid second part to make a dough;
- h) optionally, placing the dough in a mould or cavity by hand manipulation or injection; and
- i) allowing the dough to set and harden.

A particularly preferred method introduces an excess of initiator into the suspension polymerization step b) and/or the emulsion polymerization step c) so that residual initiator is encapsulated within the acrylic polymer bead particles and/or the emulsion polymerized microparticles. However, alternatively, initiator can also be added subsequently to the acrylic polymer composition first part in step e).

In a preferred embodiment, of any aspect of the present invention, a two part composition comprises an acrylic composition first part which typically comprises a first sub-population of polymer beads (usually with mean particle size of about 10-200 µm and usually PMMA) with encapsulated and/or adsorbed radiopacifying filler, a second sub-population of emulsion polymerized acrylic microparticles and, optionally, one or more further subpopulation(s) of emulsion polymerized acrylic microparticles and/or acrylic polymer beads, and a small amount of polymerization initiator such as dibenzoyl peroxide (BPO), usually also encapsulated within a PMMA bead sub-population, but which can also be added as a separate component. The second liquid part is usually a monomer, typically methyl methacrylate (MMA), which may also contain a polymerization activator such as N, N-dimethyl-p-toluidine (a tertiary amine) (DMPT) and an inhibitor such as hydroquinone (HQ) to prevent the monomer from spontaneously polymerising. Typically, a second sub-population(s) of acrylic polymer particles, which may be acrylic polymer bead particles or emulsion polymerized microparticles, have a lower average particle size than the average particle size of the first sub-population of beads having encapsulated and/or adsorbed radiopacifying filler.

When the two parts are mixed together, the first, second and optionally further sub-populations of acrylic polymer particles are wetted with monomer, solvated and begin to dissolve. The second sub-population herein dissolves at a faster rate than at least the first sub-population. The solvated polymer particles release dibenzoyl peroxide initiator into the monomer which interacts with activator, if present, to produce radicals that react with the monomer and initiate room temperature addition polymerization of the monomer. The mixture starts out as a relatively low viscosity cement and progresses to a stiffer and stiffer system that eventually hardens completely to its final set composition.

This constantly changing viscosity of the cement is characterised by dough and set times and maximum exotherm temperature attained, as defined by BS ISO 5833:2002. The dough time is considered to be the length of time following the start of mixing for the cement to achieve a dough-like mass that does not adhere to a gloved finger when gently touched. The set time is considered to be the time taken to reach a temperature midway between ambient and maximum.

The dough and set times and maximum exotherm temperatures are very important parameters that determine how the hardenable compositions are to be used. Compositions hardenable at room temperature (so-called "self-curing" or "cold-curing" systems) have dough times that are typically 4 to 10 minutes and set times that are typically 10 to 25 minutes in duration. These parameters effectively define the time period available for the operator to manipulate the dough in the desired fashion, for example pressing into a denture mould for denture base manufacture, or pressing into a bone cavity during hip repair or replacement or injecting into a vertebral cavity during spinal surgery. It may be advantageous to maximise the working time available to the operator. This should ideally be achieved without an increase in the set time as this defines the end point for the cementing or fixing operation. This therefore focuses attention on shortening the dough time. The dough time is determined by the rate at which the combination of liquid components rises in viscosity immediately after mixing and is controlled by a number of factors, such as polymer bead particle size and shape, polymer molecular weight, and polymer composition.

Polymer Beads

Preferably, as mentioned above, the acrylic polymer particle sub-populations may be or are polymer beads. Such beads are preferably not formed of emulsion polymerized particles but are preferably produced by conventional non-emulsion polymer processing. Such polymer beads are well known to the skilled person in the field of acrylic polymer compositions and may, for example, be those made by bulk, solution or suspension polymerization. Typically, the beads are made by suspension polymerization.

The term beads as used herein is not meant to be interpreted restrictively unless indicated otherwise and refers to a discrete polymer particle of any suitable size, shape and surface texture. In the context of the present application however, the term bead may be used to differentiate this type of acrylic polymer particle from emulsion polymerized microparticles or larger particles formed from coalesced emulsion polymerized microparticles.

Emulsion Polymerized Microparticles

Typically, as mentioned above, the acrylic polymer particle sub-populations may be or are emulsion polymerized microparticles. Typically, the emulsion polymerized microparticles are in the form of a network of coalesced emulsion polymerized microparticles.

For the avoidance of doubt, by coalesced is not meant that the individual microparticles merge completely but that they join together sufficiently to form a larger type of particle. Typically, the microparticles come into close contact but also retain individual character.

Preferably, the Z-average particle size of the emulsion polymerized microparticles is less than 2 μm as determined by light scattering using a Malvern Zetasizer nano series S particle size analyzer (adding one drop of emulsion to 1 ml of de-ionised water in a measurement cuvette, allowing the test sample to equilibrate at 25° C. and determining Z-average particle size using the software provided by the instrument), more preferably, less than 1 μm most preferably, less than 0.8 μm, especially, less than 0.5 μm. A preferred Z-average particle size range for the emulsion polymerized microparticles is between 0.01-2 μm, more preferably, 0.02-1 μm, most preferably, 0.05-0.5 μm, especially 0.1-0.45 μm, as determined by light scattering using a Malvern Zetasizer as above.

Typically, the emulsion polymerized microparticles may be single stage or multistage i.e. the so called core/shell particles. In this regard, it may be adequate to use a single monomer such as methyl methacrylate for making seed, core and shell. In this case, particularly if the composition and molecular weight of the seed, core and shell are designed to be the same, standard single stage emulsion polymerization techniques known to the skilled person could be deployed. However, to obtain emulsion polymerized microparticles that display some control over their structure, particularly their composition, particle size and molecular weight, it is preferable to use the multistage core-shell emulsion polymerization approach.

For manufacturing core-shell particles by emulsion polymerization, it is convenient to employ the widely used method of initially forming seed particles, which then act as nuclei for further growth, i.e. to produce a polymeric core and then shell. The concept is described in more detail by V. L. Dimonie, et al, "Emulsion Polymerization and Emulsion Polymers", P. A. Lovell and M. S. El-Aasser, Eds, John Wiley & Sons Ltd, Chapter 9, pages 294-326, (1997). The seed particles may be formed and stabilised using either emulsifier-free techniques (i.e., particle stabilisation arising from the use of ionic water-soluble initiators, such as potassium, sodium or ammonium persulphate) or through using emulsifiers. Once the seed particles are formed, the core and shell are formed from sequential addition of further aliquots of monomer and initiator.

Typically, the emulsion polymerized microparticles are formed by drying of the liquid emulsion to form a powder.

The preferred means of drying the emulsion polymerized microparticles is to use spray drying. However, other methods of direct drying of the emulsion polymerized microparticles are also possible e.g., vacuum paddle or rotational drying. Additionally, the emulsion could be coagulated through use of ionic salts (e.g., magnesium sulphate, calcium chloride, aluminium sulphate, etc.), then filtered, washed and dried. All these techniques will cause the emulsion polymerized microparticles to coalesce into larger particles. Surprisingly, it has been found that the use of these larger particles in a hardenable composition significantly shortens the dough time. The use of particles so formed had not been expected to cause such an improvement. The coalescing of the emulsion polymerized microparticles does not cause them to merge completely and instead they form a network of joined microparticles. These drying techniques and the prior emulsion polymerization allow very careful control of the emulsion polymerized microparticle size and the larger coalesced particle size which gives easy reproducibility and reduces batch to batch variation.

By drying is meant reduction of the moisture content of the emulsion polymerized microparticles to <10% w/w, more preferably, <5% w/w, most preferably, <2% w/w.

The % wt solids content of the emulsion before drying is typically, between 5 and 45% wt, more typically, between 7.5 and 40% wt, preferably, between 10 and 37.5% wt.

Typically, the size of the larger coalesced particles is not thought to be critical but will clearly be in excess of the size of the emulsion polymerized microparticles. Typically, the larger coalesced particles have an average particle size of 1-300 μm, more typically, 2-200 μm, most typically, 5-200 μm, especially, 5-150 μm. However, the size of the larger coalesced particles is thought to be less critical than the size of the emulsion polymerized microparticles which make up their structure.

Advantageously, the emulsion polymerized microparticles form a porous larger coalesced particle, more preferably, a microporous larger coalesced particle.

By microporous in the present invention is included particles having an average pore size of between 0.1 and 2000 nm, more preferably, between 1-1000 nm, most preferably, 10-500 nm. Pore size may be determined by scanning electron microscopy (SEM) according to the following test method: Sprinkle the sample of acrylic polymer particles onto a conducting self-adhesive carbon tab on a standard aluminium SEM stub. Coat the sample with a thin layer of metal (Pt) by vacuum metallization to avoid charging in the SEM instrument. SEM images may be taken using a Hitachi S4500 Field Emission SEM using accelerating voltage of 3 kV and working distance of 20 mm. Imaging is carried out on several particles and representative images obtained at different magnifications Typically, the network of coalesced emulsion polymerized microparticles is itself a porous larger coalesced particle which typically has a large surface area resulting at least in part from the presence of voids in said particles. Typically, these larger coalesced particles have an average surface area of between 1 and 100 $m^2/g$, more preferably, between 10 and 100 $m^2/g$, most preferably between 15 and 50 $m^2/g$.

Thus the surface area is typically, at least 5 $m^2/g$, more typically, at least 10 $m^2/g$, most typically, at least 15 $m^2/g$. The surface area herein may be determined by the method of Brunauer-Emmett-Teller (BET) according to ISO 9277: 2010.

Typically, these larger coalesced particles have an average total pore volume of between 0.005 and 0.5 $cm^3/g$, more preferably, between 0.015 and 0.2 $cm^3/g$, most preferably, between 0.025 and 0.1 $cm^3/g$. Thus the total pore volume in the particle is typically at least 0.01 $cm^3/g$, more typically, at least 0.020 $cm^3/g$, most typically, at least 0.025 $cm^3/g$. The total pore volume herein may be determined by the method of Barrett-Joyner-Halenda (BJH) according DIN 66134.

Accordingly, in one embodiment the larger coalesced particle as measured in accordance with the above methods has an average surface area of between 1 and 100 $m^2/g$, more preferably, between 10 and 100 $m^2/g$, most preferably between 15 and 50 $m^2/g$ and/or at least 5 $m^2/g$, more typically, at least 10 $m^2/g$, most typically, at least 15 $m^2/g$ and an average total pore volume of between 0.005 and 0.5 $cm^3/g$, more preferably, between 0.015 and 0.2 $cm^3/g$, most preferably, between 0.025 and 0.1 cm$^3$/g and/or at least 0.01 cm$^3$/g, more typically, at least 0.020 cm$^3$/g, most typically, at least 0.025 cm$^3$/g.

The core shell (C:S) ratio of the emulsion polymerized microparticles is typically, between C:S 95:5% wt and C:S 40:60% wt, more typically, between C:S 90:10% wt and C:S 50:50% wt, preferably, between C:S 85:15% wt and C:S 70:30% wt.

Typically, as mentioned above, the emulsion polymerized microparticles are coalesced by drying a polymer emulsion of the microparticles such as by spray drying, paddle drying, oven drying or drying following coagulation and filtration. Advantageously, spray drying allows easy control of the final particle size by varying the spray droplet size appropriately. In any case, the drying step causes the emulsion polymerized microparticles to coalesce and form a network of emulsion polymerized microparticles, typically giving a porous larger coalesced particle. Typically, it has been found that emulsion polymerized microparticles can coalesce into a loosely hexagonal close packed matrix generally in the same plane but, in the present case, due to holes and imperfections in this arrangement and also the three dimensional structure of the particulate network, a porous macrostructure results. The emulsion polymerized microparticles are also, inevitably, present in the coalesced network of the larger powder particle, in smaller clusters and also as individual particles. The temperature of the spray drying and in particular the spray drier outlet temperature is preferably such as to avoid the primary particles of the emulsion sintering together to form fused or partially fused aggregates and this is usually achievable by ensuring that the drier outlet temperature is not more than 15° C. above the polymer glass transition temperature, Tg.

Advantageously, as mentioned above, the emulsion polymerized microparticles in the form of a network of coalesced emulsion polymerized microparticles are microporous. The microporous nature of the larger coalesced particle means that they are more readily solvated in the liquid second part than a solid non-porous particle. This means that the second sub-population is further preferentially solvated in the liquid second part over the first sub-population of acrylic polymer particles having radiopacifier encapsulated within and/or adsorbed.

The average particle size of the larger coalesced particle will be bigger than the average particle size of the emulsion polymerized microparticles from which it is formed. However, due to the nature of the larger particle the microparticles which make up the larger particle are still substantially present.

For the avoidance of doubt, any reference herein to the average particle size of the emulsion polymerized microparticles or the average particle size of a sub-population of emulsion polymerised microparticles is with regard to the emulsion polymerized microparticles themselves and not the average particle size of any larger particle formed of a network of coalesced microparticles that may be the form in which the microparticles are present.

Polymer and Other Component Amounts

Typically, the acrylic polymer particle sub-populations of the invention form at least 98% w/w of the undissolved polymer present in the composition prior to mixing, more preferably, at least 99% w/w, most preferably, approximately 100% w/w of the undissolved polymer present in the composition prior to mixing. Upon mixing the monomer polymerizes and causes the mixed composition to form a cement which gradually hardens eventually setting to a solid. Some polymer, preferably, acrylic polymer as defined herein may also be dissolved in the monomer composition prior to mixing. Such levels of dissolved polymer are typically in the range 0-60% w/w in the acrylic monomer component, more typically 10-30% w/w.

The acrylic polymer particle sub-populations together with encapsulated and/or adsorbed radiopacifying filler may typically form between 50-99.9% w/w of the acrylic polymer composition first part, more preferably, 60-97.5% w/w, most preferably, 65-94.5% w/w. The balance is generally made up of other solids which may be fillers, pigments, dyestuffs, catalysts, non-encapsulated radiopacifying filler and initiator.

The ratio of emulsion polymerized microparticles to non-emulsion polymerized acrylic polymer particles such as beads when both are present in the sub-populations varies depending on the final application. Nevertheless, it is advantageous in some applications such as bone cements to have a ratio thereof of between 2:98 to 50:50 w/w thereof, more preferably, 3:97 to 40:60 w/w, most preferably, 5:95 to 30:70 w/w. However, no restriction should be taken hereby and other emulsion polymerized microparticle ratios are also possible such as 0% w/w emulsion polymerized microparticles. It is also possible for the sub-populations to constitute up to 100% w/w bead polymer particles i.e. 0% emulsion polymerized microparticles.

The liquid second part may include in addition to monomer, water or other solvent as additional liquid components which in any case are sufficient to provide a liquid carrier for the other components which may include other polymer composition components known to the skilled to the skilled person such as acrylic polymer, initiator (although this is not preferred and only if activator is absent,), fillers, pigments, dyestuffs, catalysts, accelerators, plasticisers etc. In this regard, although it is possible to use an initiator paste in a liquid carrier such as water or organic solvent, optionally in the presence of plasticizer to form a further part of the composition, it is more typical to have acrylic monomer as the only liquid carrier in the composition, optionally with acrylic polymer particles dissolved therein and with other components added such as accelerators, fillers, dyes etc. Generally, the amount of monomer in the hardenable composition, whether in the second, or further part, is in the range 10-70% w/w, more typically 15-60% w/w, more preferably 20-50% w/w. Typically, the monomer is present at these overall compositional levels in the second part.

When both monomer and acrylic polymer dissolved resin or particles form the bulk of the second liquid part, or further liquid parts, the ratio of acrylic monomer:polymer is in the range 99:1 to 40:60 w/w.

The acrylic polymer composition first part is generally present as a dry powder prior to mixing with the monomer composition. The weight ratio of dry powder component to monomer component is generally <3:1, more preferably, <2.5:1, most preferably, < 2.2:1. Typically, the weight ratio is in the range 2.15-1.85:1.

Typically, the level of filler in the hardenable acrylic composition of the invention whether radiopacifying or otherwise is 1-55% w/w of the acrylic composition, more preferably, 5-45% w/w, most preferably, 6.5-35% w/w. The filler may be present in any one of the parts or may be distributed in two or more parts.

Preferably, at least 90% w/w of the total radiopacifying filler in the composition is present in the acrylic polymer composition first part, more preferably, at least 95% w/w, most preferably, at least 99% w/w. In preferred embodiments, substantially all the radiopacifying filler in the composition is present in the acrylic polymer composition first part. Typically, therefore, the radiopacifying filler is present in only one part of the composition.

Typically, all or substantially all of the said acrylic monomer component and the said radiopacifying filler are located in separate parts of the composition so that the radiopacifying filler is not substantially present or is reduced in the polymer matrix of the final hardened material.

Preferably, at least 90% w/w of the total first or further (if present) sub-population acrylic polymer particles with encapsulated and/or adsorbed radiopacifying filler in the composition are present in the acrylic polymer composition first part, more preferably, at least 95% w/w, most preferably, at least 99% w/w. In preferred embodiments, substantially all the first or further (if present) sub-population acrylic polymer particles with encapsulated and/or adsorbed radiopacifying filler in the composition are present in the acrylic polymer composition first part. Typically, therefore, the acrylic polymer particle sub-population(s) with encapsulated and/or adsorbed radiopacifying filler are present in only one part of the composition prior to mixing.

Typically, all or substantially all of the said acrylic monomer component and the said polymer particle sub-population(s) with encapsulated and/or adsorbed radiopacifying filler are located in separate parts of the said composition so that encapsulated and or adsorbed radiopacifying filler is not released into the monomer component prior to mixing and therefore released radiopacifying filler presence in the polymer matrix of the final hardened material is reduced or avoided.

Preferably, at least 90% w/w of the total second or further (if present) sub-population acrylic polymer particles with lower average particle size in the composition are present in the acrylic polymer composition first part, more preferably, at least 95% w/w, most preferably, at least 99% w/w. In preferred embodiments, substantially all the second or further (if present) sub-population acrylic polymer particles with lower average particle size than the first sub-population in the composition are present in the acrylic polymer composition first part. Typically, therefore, the second or further (if present) sub-population acrylic polymer particles with lower average particle size than the first sub-population are present in only one part of the composition prior to mixing.

Typically, all or substantially all of the said acrylic monomer component and the said polymer particle sub-populations having lower average particle size are located in separate parts of the said composition so that encapsulated and or adsorbed radiopacifying filler release into the monomer component after mixing is retarded or avoided and therefore released radiopacifying filler presence in the polymer matrix of the final hardened material is reduced.

Preferably, at least 90% w/w of the total emulsion polymerized microparticles present in the composition whether in the second or further sub-populations are present in the acrylic polymer composition first part, more preferably, at least 95% w/w, most preferably, at least 99% w/w. In preferred embodiments, substantially all the emulsion polymerized microparticles in the composition are present in the acrylic polymer composition first part. Typically, therefore, the emulsion polymerized microparticles are present in only one part of the composition.

Preferably, at least 90% w/w of the total acrylic polymer bead with encapsulated and/or adsorbed radiopacifying filler in the composition whether in the first or further sub-populations is present in the acrylic polymer composition first part, more preferably, at least 95% w/w, most preferably, at least 99% w/w. In preferred embodiments, substantially all the acrylic polymer bead with encapsulated and/or adsorbed radiopacifying filler in the composition is present in the acrylic polymer composition first part. Typically, therefore, the acrylic polymer bead with encapsulated and/or adsorbed radiopacifying filler is present in only one part of the composition.

Accelerators may be present in the unmixed composition in the range 0.1 to 5% by mass, more typically, 0.5-3% by mass.

The total level of unreacted initiator, whether residual or added, in the multi-part acrylic composition is typically, 0.1-10% w/w of the acrylic composition, preferably, 0.15-5% w/w, more preferably, 0.2-4.0% w/w.

Where initiator is used in one of the components, this may itself be encapsulated within polymer bead and/or emulsion polymerized microparticles or separately added to any parts of the composition. Although it is possible to have initiator in the liquid part with the acrylic monomer component such would only have a short shelf life. Accordingly, typically, the initiator and acrylic monomer component are located in separate parts of the composition.

Where polymer is dissolved in monomer in the liquid second part, or any further liquid parts, the polymer must preferably contain very low (e.g. <0.1% w/w) levels of residual initiator to avoid shortening of the shelf life.

The initiator may be present in acrylic polymer particles that form part of the acrylic composition. The initiator in the acrylic polymer particles may be the residual amount of unreacted initiator used in the formation of the polymer particles which is therefore the equivalent of the excess amount of initiator. Some initiator can alternatively or additionally be added as a separate component to the multi-part composition. In the emulsion polymerized microparticles or bead polymer particles, the level of residual initiator present before reaction is typically, 0.001-10% w/w polymer particle, preferably, 0.1-6% w/w, more preferably 0.1-5% w/w.

Preferably, the initiator is present at a level which will effect polymerization of the monomer component that is at least greater than 90% polymerization, more typically, greater than 93%, more typically greater than 95% polymerization.

The two or more sub-populations of acrylic polymer particles present in the composition may be present in the same part and/or in different parts. In a preferred embodiment, a first sub-population with encapsulated and/or adsorbed radiopacifying filler is present in the acrylic polymer composition first part with a second sub-population of emulsion polymerized microparticles which may or may not have encapsulated and/or adsorbed radiopacifying filler. A further polymer sub-population may be present in the liquid second part dissolved or partly dissolved in the acrylic monomer component.

The polymer components are typically in the presence of suitable other polymer composition components known to the skilled person. Such polymer composition additives include initiators, emulsifiers, catalysts, pigments, dyestuffs and fillers.

Specific Materials

Initiators that can be used to initiate the emulsion polymerization and therefore those which may form residual initiators in the composition to initiate the hardening process are persulphates, (e.g., potassium, sodium or ammonium), peroxides (e.g., hydrogen peroxide, dibenzoyl peroxide, tert-butylhydroperoxide, tert-amylhydroperoxide, di-(2-ethylhexylperoxydicarbonate or lauroyl peroxide) and azo initiators (e.g., 4,4'-azobis(4-cyanovaleric acid)).

In addition to the emulsion initiators above, a particularly preferred initiator for the hardening stage is dibenzoyl peroxide.

Initiators that can be used for conventional or emulsifier free emulsion polymerization and therefore which may be present as residual initiators include:—ionic water-soluble initiators, such as potassium, sodium or ammonium persulphate.

In addition, any one or more of the above initiators can be added to the composition independently.

In a particularly preferred embodiment, the acrylic polymer particles incorporate the initiator in their polymer matrix. The initiator may be incorporated into the polymer matrix of acrylic polymer bead particles and/or emulsion polymerized microparticles. Preferably, the initiator is incorporated in the acrylic polymer bead particles. Accordingly, in this embodiment, the initiator is not added separately to the first part of the composition.

Advantageously, the initiator for the hardenable composition can be added as excess initiator during the polymerization of the particles so that some initiator is used in the polymerization of the particles but as the particles form, the excess initiator is incorporated into the polymer matrix. Subsequently, after wetting and dissolution with monomer, the initiator is released and thus able to initiate the hardening phase. In a core/shell particle, the initiator is preferably incorporated in the outer shell i.e. during the final stage of the multistage emulsion polymerization process and, accordingly, excess initiator is used in the final shell polymerization stage. During polymerization of the polymer particle more than one initiator may also be used. In the case of multiple initiators, it is advantageous for one of the initiators to be substantially used up in the polymerization and a second initiator to be in excess and only partly used so that the excess amount of the second initiator is incorporated into the particles. This procedure may be assisted by the initiators having different half lives so that a shorter half life initiator (i.e., an initiator with a higher decomposition rate at a given temperature and reaction medium) is used up preferentially. In addition, a higher temperature can be used to drive the polymerization to completion in the presence of the first initiator whilst a lower temperature can retard polymerization of monomer in the presence of the second initiator intended as a residual initiator. However, some of the second initiator will inevitably be used up because to incorporate the initiator into the particle some polymerization must take place in the presence of the second initiator. Whether one or more initiators are used, the amount of initiator left as residue depends on the time of exposure of the initiator to polymerization conditions and reactants, and the relative reactivity to the first initiator, if present. It will be appreciated by the skilled person that the exact amount of residual initiator will be dependent on the experimental conditions and can easily be determined by trial and error and then be made reproducible by careful control of quantities of monomers and initiators and process conditions. The time of addition of the initiator in excess is also relevant to the molecular weight of the polymer. If added too early in the polymerization, the molecular weight of the particle will be reduced. Accordingly, the molecular weight required will also influence the time of addition of the initiator in excess so that the excess initiator is incorporated whilst achieving the molecular weight required for the particular application.

Preferably, step (a) of the method of production of the invention when including emulsion particles comprises seed, core and at least one shell emulsion polymerization step. A particularly preferred method introduces an excess of initiator into the emulsion polymerization step so that residual initiator is encapsulated within the emulsion particles. Preferably, in a multistage emulsion polymerization, the excess initiator is introduced during the final stage so that it is present in the outer shell of the multistage particle. However, alternatively, initiator can also be added subsequently to the acrylic polymer emulsion.

For the avoidance of doubt, by "excess initiator" is meant, the portion of initiator that is not required to complete polymerisation of the acrylic polymer particles and is available for subsequent reaction after the initial polymerization of the acrylic polymer particles is terminated.

Variation in the amount of encapsulated residual initiator or added initiator (e.g. dibenzoyl peroxide) has the effect of varying the set time of the hardenable composition. Increased initiator level results in shortened set time. Additionally, variation of the amount of accelerator (e.g. DMPT) in the acrylic monomer composition can also affect the set time. Increased accelerator concentration results in shortened set time.

Typically, herein, initiator will be present in the composition at a level of 0.1 to 5% w/w total monomer and initiator.

In compositions according to the invention other fillers may be used and these will be known to the skilled person in the art of such fields. Additionally, organic x-ray opaque monomers can be used in addition to fillers. These can be copolymerized into any of the acrylic polymer particles during their production or incorporated into the acrylic monomer composition. Typical organic x-ray opaque monomers include halogenated methacrylates or acrylates, e.g., 2,3-dibromopropyl methacrylate or 2-methacryloyloxyethyl-2,3,5-triiodobenzoate. For the avoidance of any doubt, such x-ray opaque monomers are not to be regarded as fillers or radiopacifying fillers.

Emulsifiers that can be used in the emulsion polymerization are those that are typical in conventional emulsion polymerization, including anionic (e.g., sodium dioctyl sulfosuccinate, disodium ethoxylated alcohol half ester of sulfosuccinic acid, tetrasodium N-(1,2-dicarboxy ethyl)-N-octadecyl sulfosuccinate, sodium salt of sulphated alkylphenol ethoxylates, sodium alkane sulfonate, sodium dodecyl sulphate or sodium 2-ethylhexyl sulphate), nonionic (e.g., polyethylene glycol nonylphenyl ethers, polyethylene oxide octylphenyl ethers, or di-functional ethylene oxide/propylene oxide block copolymers) or cationic emulsifiers (e.g., hexadecyltrimethylammonium bromide or alkyl polyglycoletherammonium methyl chloride). Reactive or polymerisable emulsifiers or surfactants suitable for use with acrylic emulsions can also be used, e.g., sodium dodecylallyl sulfosuccinate, styrene sodium dodecylsulfonate ether, dodecyl sodium ethylsulfonate methacrylamide, methacrylic or vinylbenzyl macromonomers of polyethylene oxide or ethylene oxide/propylene oxide block copolymers or methacryloylethylhexadecyldimethylammonium bromide.

The mixing of the further components of the invention with the liquid carrier in the liquid second part, or any further liquid parts, may be carried out by any suitable technique known to the skilled person for mixing solids or liquids with a liquid.

Preferably, in the present invention, there is at least 1 wt % of each sub-population present, more preferably, 5 wt %, most preferably, 10 wt %. For example, where there are two sub-populations the typical ratios are in the range 1-99:99-1 wt %, more typically, 10-90:90-10 wt %. For further example, where there are three types, the typical ratios are in the range 1-98:98-1:98-1 wt %, more typically, 5-90:90-5:90-5 wt %.

Preferably, the compressive strength of the solid produced by mixing the said parts in any aspect of the present invention is greater than 40 MPa, more preferably greater than 70 MPa. The typical range of compressive strengths found in the produced solid is 40-130 MPa, more preferably 70-130 MPa.

DEFINITIONS

The term "adsorbed" takes its usual meaning and means bound to the surface thereof.

The term "liquid" herein does not require definition because it is well understood by the skilled person. However, for the avoidance of doubt it also includes a flowable material having a liquid carrier such as a slurry, suspension, emulsion or paste that is thus susceptible of delivery through a syringe or caulking gun outlet by the application of pressure. Typically, the term liquid is applicable to the material or composition at least between 5 and 35° C., more typically, between 5 and 30° C.

The term "solid part" means a non-liquid or non-gaseous part and is generally a free flowing dry particulate material usually made up of one or a mixture of powder(s) and not including a liquid carrier.

By "storage stable" is meant that the monomer or liquid does not polymerize under normally acceptable storage conditions of temperature and time i.e. between 5 and 30° C. and 1 to 250 days, more typically, 15 to 25° C. and 1 to 170 days.

The term "sub-population" is generally understood by the skilled person but for the avoidance of doubt refers to a plurality of polymer particles having a specific molecular weight (MW), molecular weight distribution, porosity, nature and distribution of (co)monomer residues, average particle size, particle size distribution, the presence or absence of residual initiator and, if present, the amount and type of residual initiator and/or type as is usually produced by monomer(s) which have undergone the same polymerization process(es) together.

The term "lower" herein in the context of average particle size or the like means having a lower value but is preferably, at least 10% lower than the comparative larger value, more preferably, at least 20% lower, most preferably at least 50% lower than the larger value.

The Z-average particle size herein is determined by light scattering using a Malvern Zetasizer nano series S particle size analyzer.

The mean particle size herein may be determined using a Coulter LS230 laser diffraction instrument.

The term "microparticle" herein is meant a polymer particle having an average particle size of <10 μm, preferably <2 μm, more preferably <1 μm.

The method of manufacture of acrylic bead polymer particles is generally conventional suspension or dispersion polymerization to produce generally spherical polymer particles, or beads. However, other methods of manufacture are also possible, e.g., bulk polymerization or solution polymerization followed by evaporation of the solvent.

By acrylic polymer herein whether in relation to the acrylic polymer particles or otherwise is meant independently for each sub-population a homopolymer of a polyalkyl(alk)acrylate or (alk)acrylic acid or copolymers of a alkyl(alk)acrylate or (alk)acrylic acid with one or more other vinyl monomers. Typically, a homopolymer of methyl methacrylate or a copolymer of methyl methacrylate with one or more other vinyl monomers is used. By other vinyl monomers is included a further alkyl(alk)acrylate or (alk)acrylic acid such as ethyl methacrylate, methyl acrylate, ethyl acrylate, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, methacrylic acid or acrylic acid; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone or vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate or 1,6-hexanediol diacrylate, particularly the compatible acrylic crosslinking monomers.

Copolymers containing functionalized monomers are of special interest because they may help in dispersing non-encapsulated radiopacifying fillers into the monomer containing part. Suitable functionalized monomers are well known in the field of pigment dispersion in inks and coatings. For example, amines such as N,N-dimethylaminoethyl methacrylate, N,N-diethylaminoethyl methacrylate, t-butylaminoethyl methacrylate and acids such as methacrylic acid and acrylic acid.

Crosslinking monomers can be used to crosslink the acrylic polymer particles or one or more of the acrylic polymer particle sub-populations. For the emulsion polymerized microparticles, crosslinking may be carried out in the core and the shell, or only the core, or only the shell. Crosslinking serves the purpose of fine-tuning the properties of the hardenable multi-part acrylic composition.

The weight average molecular weight (Mw) of the emulsion polymerized microparticles is typically, between 25,000 daltons and 3,000,000 daltons, more typically, between 100,000 daltons and 1,500,000 daltons, preferably, between 250,000 and 1000000, for instance, between 250,000 and 600,000. Molecular weight may be determined for this purpose by gel permeation chromatography (GPC).

Although, the molecular weights of the polymers in the polymer components of the hardenable composition may influence the dough and work times, the invention is not restricted to any particular molecular weight. In any case, reductions in the molecular weight and/or increases in the particle size of the acrylic polymer particles can be used to increase the work time of the hardenable composition.

The weight average molecular weight (Mw) of the bead type of polymer particles, if present, is typically, between 10,000 daltons and 3,000,000 daltons, more typically, between 30,000 daltons and 1,000,000 daltons, preferably, between 50,000 and 700,000, for instance, between 60,000 and 600,000 Daltons. Molecular weight may be determined for this purpose by gel permeation chromatography (GPC).

By acrylic monomer herein is meant any one or more suitable alkyl(alk)acrylate or (alk)acrylic acid such as methyl methacrylate, ethyl methacrylate, methyl acrylate, ethyl acrylate, methacrylic acid or acrylic acid, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate or isobornyl methacrylate; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone or vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate or 1,6-hexanediol diacrylate, particularly the compatible acrylic crosslinking monomers. Alternatively, the suitable acrylic monomers may exclude ethyl methacrylate and/or n-butyl methacrylate from the foregoing. Typically, methyl methacrylate is the monomer component of the invention.

The acrylic monomer component of the invention is optionally, provided with an accompanying suitable inhibitor such as hydroquinone (HQ), methyl hydroquinone (MeHQ), 2,6-di-tertiary-butyl-4-methoxyphenol (Topanol O) and 2,4-dimethyl-6-tertiary-butyl phenol (Topanol A). The inhibitor is present to prevent the monomer from spontaneously polymerising. A suitable inhibitor is 60 ppm of hydroquinone to ensure long shelf life at room temperature.

Polymerization activators or accelerators may also be optionally present, such as N,N-dimethyl-p-toluidine (DMPT) and N,N-dihydroxyethyl-p-toluidine (DHEPT) (both tertiary amines) or organic-soluble transition metal catalysts. The presence of activators or accelerators depends upon the final application. Where "cold-cure" is necessary such as in dental or bone cement applications, an accelerator is usually necessary. However, for some applications the use of heat in "heat-cure" systems is also possible. For instance, dentures can be activated by heat. When present in the composition, accelerator is typically present at a level that will effectively activate the polymerisation reaction in the presence of initiator, typically, this is at a level of 0.1 to 5% w/w total monomer and accelerator.

By alkyl herein is meant $C_1$-$C_{18}$ alkyl wherein the term alkyl and alk encompasses cycloalkyl and hydroxyl functional $C_1$-$C_{18}$ alkyl. By alk herein is meant $C_0$-$C_8$ alk.

In one preferred embodiment, the acrylic polymer composition first part containing the acrylic polymer particles having encapsulated and/or adsorbed radiopacifying filler comprises emulsion polymerized microparticles and only a single further sub-population of acrylic polymer bead particle, the former generally to control the dough time and the latter to generally control the working time.

By "acrylic composition" is meant a composition where at least 50% of the total monomer and monomer residues present are present as or derived from one or more of the above defined acrylic monomers, more typically, is meant at least 70%, most typically, 95% or especially, 99% of the total monomer or monomer residues present.

In a preferred two-part embodiment of the invention acrylic polymer composition first part comprises emulsion polymerized microparticles, a sub-population of acrylic polymer bead particles with encapsulated and/or adsorbed radiopacifying filler (preferably PMMA bead) and initiator and the second part comprises acrylic monomer (preferably MMA monomer) and accelerator. In this embodiment the Z-average particle size of the emulsion polymerized microparticles is lower than the acrylic polymer bead mean particle size with encapsulated and/or adsorbed radiopacifying filler.

In a further preferred two-part embodiment of the invention the acrylic polymer composition first part comprises emulsion polymerized microparticles, a sub-population of acrylic polymer bead particles with encapsulated and/or adsorbed radiopacifying filler and initiator and the second part comprises a solution of initiator-free acrylic polymer (preferably PMMA), in acrylic monomer (preferably MMA) with accelerator. In this embodiment the Z-average particle size of the emulsion polymerized microparticles is lower than the acrylic polymer bead mean particle size with encapsulated and/or adsorbed radiopacifying filler.

In a further preferred two-part embodiment of the invention the acrylic polymer composition first part comprises a first sub-population of acrylic polymer bead particles, a sub-population of acrylic polymer bead particle with encapsulated and/or adsorbed radiopacifying filler and initiator (optionally, encapsulated in one or both bead populations) and the second part comprises a solution of initiator-free acrylic polymer (preferably PMMA), in acrylic monomer (preferably MMA) with accelerator. In this embodiment the mean particle size of the acrylic polymer bead particles is lower than the acrylic polymer bead mean particle size with encapsulated and/or adsorbed radiopacifying filler.

In a further preferred embodiment of the invention the first part comprises a initiator-free acrylic polymer bead with encapsulated and/or adsorbed radiopacifying filler (preferably PMMA bead), emulsion polymerized acrylic polymer microparticles, acrylic monomer (preferably, MMA monomer) and accelerator and the second part comprises an initiator paste. Initiator pastes are available commercially usually as a mixture with water or plasticiser. In this embodiment the Z-average particle size of the emulsion polymerized acrylic polymer particles is lower than the mean particle size of the acrylic polymer bead particle with encapsulated and/or adsorbed radiopacifying filler Advantageously, in the present invention the monomer and initiator are kept in separate parts of the multi-part composition so that monomer is added from one part when unreacted initiator is present in another part and so that initiator is added from the other part when no unreacted initiator but instead monomer is present in the one part.

Notwithstanding the foregoing, a particularly advantageous application of the acrylic composition of the aspects of the invention is its use as bone cement compositions. Such compositions are used in vertebroplasty. A similar application for the compositions of the present invention is dental repairs.

Emulsion polymerized microparticles are well known in the field of impact modifiers. For this reason an impact modifier such as butadiene or butyl acrylate is typically introduced as a comonomer into one of the shells of the multistage core shell particle. However, in the multi-part compositions of the present invention, an impact modifier may not be required. Accordingly, the emulsion polymerized microparticles of the present invention may be free from impact modifier co-monomer residues.

The acrylic composition first part of the present invention containing the encapsulated and/or adsorbed radiopacifying filler may be provided separately as a dry powder with or without added further components as defined herein for later use as a dry powder part in a hardenable composition.

Accordingly, according to a further aspect of the present invention there is provided a solid acrylic polymer composition comprising a first sub-population of emulsion or non-emulsion polymerized acrylic polymer particles, and at least one further sub-population of emulsion or non-emulsion polymerized acrylic polymer particles and characterized in that there is a polymerization initiator in the acrylic polymer composition at a level sufficient to cause the acrylic polymer composition to harden upon contact with a reactive monomer liquid and in that radiopacifying filler is encapsulated and/or adsorbed in the first sub-population of the acrylic polymer particles and wherein one or more of the further sub-population(s) of acrylic polymer particles in the composition have a lower average particle size than the first sub-population having encapsulated and/or adsorbed radiopacifying filler.

There is no particular temperature limitation on the use of the present invention. Generally, however, it is used at temperatures acceptable to the operator i.e. temperatures found during normal working conditions that may be encountered indoors or outdoors by the operator, for example 5-40° C. and atmospheric pressure and/or applied syringe pressure.

For medical applications such as bone cement and dentistry to which the compositions of the invention are mainly directed the composition is biocompatible and in particular hardens to a solid cement or adhesive that is biocompatible in situ. Accordingly, the composition of the invention finds particularly advantageous utility as a medical implant material such as a bone cement or a solid effective in dental applications. Accordingly, the multi-part composition is typically a bone cement composition or dental composition.

According to a further aspect of the present invention there is provided a medical implant material produced from mixing a multi-part acrylic composition according to the present invention.

According to a still further aspect of the present invention there is provided a multi-part composition according to any aspect of the present invention for use in surgery, more particularly for use in the treatment of human or animal bone or teeth.

According to a still further aspect of the present invention there is provided a multi-part composition according to any aspect of the present invention for use in the replacement or partial replacement of human or animal bone.

According to a still further aspect of the present invention there is provided a multi-part composition according to any aspect of the present invention for use dentistry, more particularly in the treatment of human teeth or animal teeth or for use in veterinary surgery, more particularly, for use in the treatment of hoof, nail or horn.

According to a still further aspect of the present invention there is provided a multi-part composition according to any aspect of the present invention for use in the replacement or partial replacement of human teeth or animal teeth, hoof, nail or horn.

A general procedure for mixing the parts of the hardenable composition of the invention is described as follows: Before mixing, the two components are equilibrated for a suitable period, typically, 1 hour or more at a temperature of 5-40° C., more typically, 10-35° C., most typically, 15-3° C. Acrylic polymer composition first part is mixed with a suitable amount of liquid second part and, if present, any other liquid parts according to the ratios defined herein. Mixing is then carried out at the equilibrated temperature for at least 5, more typically, at least 20, most typically, at least 30 seconds. When the dough time has been reached, the doughed material is packed into place such as moulds preconditioned at an appropriate temperature generally in the range of the epuilibration temperatures above and allowed to exotherm and harden. Alternatively, the doughed material may be implanted within some other cavity, such as bone and allowed to exotherm and harden.

The mixing of the two components and subsequent reaction can be carried out at the equilibration temperatures. The skilled person will be aware of the effect of temperature on the dough and set times. Higher mixing temperature leads to shorter dough and set times and vice versa for lower mixing temperature.

BRIEF DESCIPTION OF THE DRAWINGS

Embodiments of the invention will now be described with reference to the accompanying figures and examples in which:

FIG. 1 shows the SEM image of the spray dried powder according to the invention; and FIG. 2 shows the SEM image of a bead polymer.

EXAMPLES

Characterisation Techniques

The Z-average particle size of the emulsion polymerized microparticles is determined using a Malvern Zetasizer nano series S particle size analyzer.

The particle size (d10, d50, d90) of the powder produced from spray drying of the emulsion polymerized microparticles is determined by a Malvern Mastersizer 2000 particle size analyser.

d10, d50, d90 are standard "percentile" readings from the particle size analysis.

d50 is the size in microns at which 50% of the sample is smaller and 50% is larger.

d10 is the size of particle below which 10% of the sample lies.

d90 is the size of particle below which 90% of the sample lies.

Reduced viscosity (RV, dl/g) is measured in chloroform (1 wt % solution) using an Ubbelohde viscometer type OB at 25° C.

w/w % residual dibenzoyl peroxide content is determined by a titration method.

The mean particle size of acrylic polymer beads is determined using a Coulter LS230 laser diffraction instrument.

Dough time is measured according to BS ISO 5833:2002.

Flexural strength of the hardenable compositions was determined by a three-point bend test according to ISO 1567:1997.

Determination of surface area is by the method of Brunauer-Emmett-Teller (BET) according to ISO 9277: 2010 using a Micromeritics Tristar II 3020 instrument operating at room temperature and using nitrogen as the absorptive gas.

Determination of pore volume is by the method of Barrett-Joyner-Halenda (BJH) according to DIN 66134 using a Micromeritics Tristar II 3020 instrument operating at room temperature and using nitrogen as the absorptive gas.

Pore size is determined by scanning electron microscopy (SEM) according to the following test method: Sprinkle the sample of acrylic polymer particles onto a conducting self-adhesive carbon tab on a standard aluminium SEM stub. Coat the sample with a thin layer of metal (Pt) by vacuum metallization to avoid charging in the SEM instrument. SEM images are taken using a Hitachi S4500 Field Emission SEM using accelerating voltage of 3 kV and working distance of 20 mm. Imaging is carried out on several particles and representative images obtained at different magnifications Preparative Example 1

Use of emulsion polymerization and spray drying to produce coalesced emulsion polymerized microparticles of poly(methyl methacrylate) (PMMA).

Emulsion Polymerization 1.0 liter of deionised water is added to a five-liter round bottomed glass flask fitted with a nitrogen inlet, condenser and electrically operated stainless steel paddle stirrer. The water is heated to 82° C. by means of an electric heating mantle whilst stirring at 392 min$^{-1}$. A flow of nitrogen is passed through the vapour space of the flask above the surface of the liquid.

A monomer mixture is prepared consisting of 500 grams of methyl methacrylate, 1.85 grams of 1-dodecanethiol content and 5.0 grams of 75% active sodium dioctylsulphosuccinate emulsifier (trade name: Aerosol™ OT). These components are mixed before use.

With the temperature of the water at 82° C., a polymer seed (Stage 1) is prepared by adding 50 grams of the monomer mixture to the flask followed by 10 milliliters of a 2 wt % solution of potassium persulphate in deionised water. Following a slight exotherm, the reaction proceeds for thirty minutes until the temperature returns to 82° C.

The core is then grown over the polymer seed particles (Stage 2) by firstly adding 20 milliliters of a 2 wt % solution of potassium persulphate in deionised water to the flask followed by continuous addition of 350 grams of the monomer mixture over approximately 35 minutes using a peristaltic pump. The reaction proceeds for a further fifteen minutes after the completion of the monomer mixture addition until the temperature returns to 82° C.

30.0 grams of 70% active benzoyl peroxide are dissolved in the remaining 100 grams of monomer mixture. This produces a residual benzoyl peroxide (BPO) content of approximately 2 wt % in the polymer product.

The BPO-containing shell is then grown over the core (Stage 3) by firstly adding five milliliters of a 2 wt % solution of potassium persulphate in deionised water to the flask followed by continuous addition of the monomer mixture containing added BPO over approximately 10 minutes using a peristaltic pump. The reaction proceeds for a further fifteen minutes after all the monomer mixture has been added until the temperature has returned to 82° C.

The reactor contents are then cooled to below 40° C. and filtered through a 150 micron screen. The resultant acrylic polymer emulsion has a reduced viscosity of 2.09 dl/g and a Z-average particle size of 215 nm.

Spray Drying

The emulsion is isolated as a powder by spray drying using a LabPlant™ SD05 laboratory spray dryer. The inlet temperature is 135° C., the outlet temperature is 80° C., the latex feed rate is set at 15, a 1.0 mm jet size is employed and the maximum settings for airflow rate and air compressor pressure are used.

This produces a powder with particle size d10=8.6 microns, d50=25.9 microns, d90=62.9 microns and residual benzoyl peroxide of 2.02% w/w.

Preparative Example 2

Preparation of acrylic polymer beads containing approximately 40% w/w of encapsulated and/or adsorbed X-ray opacifying filler for use in preparing a hardenable composition.

The preparation of acrylic beads containing encapsulated and/or adsorbed barium sulphate is carried out in a two-step process. Firstly, the barium sulphate (from Sachtleben Chemie GmbH) is dispersed in a syrup prepared from dissolving polymer in monomer, followed by the transformation of the dispersion into barium sulphate-filled acrylic polymer beads by suspension polymerization.

A 20% wt solution of poly(methyl methacrylate-co-N,N'-dimethylamino ethyl methacrylate) (poly(MMA-co-DMAEMA) (RV=0.5 dl/g) in MMA is prepared by dissolving 100 grams of the poly(MMA-co-DMAEMA) in 400 g of MMA at room temperature. 300 grams of this syrup is transferred to a 2 liter glass flask equipped with stainless steel anchor-type stirrer and 400 grams of barium sulphate (medical grade) is added. The flask and contents are weighed and the weight recorded. The mixture is then stirred at room temperature for 5 hours at a stirrer speed of 1500-1900 rpm. 300 grams of MMA monomer is then added and stirring is continued at 1500 rpm for a further 40 minutes. The flask is reweighed and the reduction in weight due to evaporation of MMA calculated. The calculated amount of evaporated MMA is then added to the flask along with 10 grams of benzoyl peroxide (75% active) initiator and the mixture is stirred at 1500 rpm for 15 minutes at room temperature. This forms the organic phase of the suspension polymerization.

Separately, the aqueous phase of the suspension polymerization is prepared by adding 2000 ml of deionized water and 8 grams of hydroxyethyl cellulose powder (Natrosol HEC 250HR from Aqualon Ltd) to a 5 liter glass flask containing a stainless steel anchor-type stirrer. The flask contents are stirred at 400 rpm and heated to 40° C. to dissolve the hydroxyethyl cellulose. The organic phase containing the barium sulphate dispersed in a monomer/polymer syrup is then added and the contents of the reactor flask heated to 82° C. using a water bath. The polymerization is continued at 82° C. until the reactor contents experience an exotherm, typically to approximately 90-92° C. The reactor flask is then cooled and the resultant acrylic polymer beads containing encapsulated and/or adsorbed barium sulphate are filtered, washed with deionized water, dried in an air circulating oven overnight at 50° C. and sieved through a 300 micron mesh. The resultant product has an ash content of 40.2% w/w, residual benzoyl peroxide content of 1.1% w/w, mean particle size of 75 microns. The ash content represents the amount of encapsulated and/or adsorbed barium sulphate in the acrylic polymer beads.

Preparative Example 3

Preparative example 2 was repeated except that the amount of encapsulated and/or adsorbed barium sulphate in the acrylic polymer beads was approximately 30% w/w.

A 20% wt solution of poly(methyl methacrylate-co-N,N'-dimethylamino ethyl methacrylate) (poly(MMA-co-DMAEMA) (RV=0.5 dl/g) in MMA is prepared by dissolving 100 grams of the poly(MMA-co-DMAEMA) in 400 grams of MMA at room temperature. 300 grams of this syrup is transferred to a 2 liter glass flask equipped with stainless steel anchor-type stirrer and 300 grams of barium sulphate (medical grade) is added. The flask and contents are weighed and the weight recorded. The mixture is then stirred at room temperature for 5 hours at a stirrer speed of 1500-1900 rpm. 400 grams of MMA monomer is then added and stirring is continued at 1500 rpm for a further 40 minutes. The flask is reweighed and the reduction in weight due to evaporation of MMA calculated. The calculated amount of evaporated MMA is then added to the flask along with 10 grams of benzoyl peroxide (75% active) initiator and the mixture is stirred at 1500 rpm for 15 minutes at room temperature. This forms the organic phase of the suspension polymerization, which was then carried out in the same way as example 2. The resultant product has an ash content of 29.2% w/w, residual benzoyl peroxide content of 1.18% w/w, mean particle size of 78 microns. The ash content represents the amount of encapsulated and/or adsorbed barium sulphate in the acrylic polymer beads.

Example 1

This example describes the blending of spray dried emulsion polymer of preparative example 1 with acrylic polymer beads containing encapsulated and/or adsorbed X-ray opacifying filler of preparative example 2 and a portion of unfilled acrylic polymer beads to firstly prepare a solid component and then a hardenable composition.

A general lab scale method of blending spray dried emulsion powder with acrylic polymer beads is to use a tumble blending approach in a suitable container. The container is typically filled to three quarters of the total volume and the blending time is typically 15 to 30 minutes. 3.6 grams of the spray dried emulsion powder of preparative example 1, 15.0 grams of the acrylic polymer beads containing encapsulated and adsorbed X-ray opacifying filler of preparative example 2 and 1.4 grams of unfilled poly(methyl methacrylate) (PMMA) beads of mean diameter 75 microns are blended together according to the above method to form a solid component.

The preparation of a hardenable composition is described as follows: Before mixing, the solid and liquid components are equilibrated for at least 10 hours in an incubator at 23° C. 20.0 g of the solid component is placed into a polypropylene beaker followed by 10.0 ml (9.40 grams) of a liquid component comprising methyl methacrylate (MMA) monomer containing 60 ppm of hydroquinone (HQ) inhibitor and 1% w/w with respect to MMA of N,N-dimethyl-para-toluidine (DMPT) accelerator. Hand mixing is then carried out at 23° C. for 30 seconds using a metal spatula, whereupon the material is covered and left to stand. Periodically, the material is assessed for initial mix consistency and dough time determined. For preparing specimens for mechanical testing, doughed material is packed into moulds preconditioned at 23° C. and allowed to harden. The amount of barium sulphate in the total mixture is 20.4% w/w. The flexural strength of the resultant material is 75.0 MPa.

Example 2

This example describes the blending of spray dried emulsion polymer of preparative example 1 with a mixture of the acrylic polymer beads containing encapsulated and/or adsorbed X-ray opacifying filler of preparative examples 2 and 3 to firstly prepare a solid component and then a hardenable composition.

Thus, 3.6 grams of the spray dried emulsion powder of preparative example 1, 10.82 grams of the acrylic polymer beads containing encapsulated and/or adsorbed X-ray opacifying filler of preparative example 2 and 5.58 grams of the acrylic polymer beads containing encapsulated and/or adsorbed X-ray opacifying filler of preparative example 3 are blended together according to the method of example 1 to form a solid component.

The preparation of a hardenable composition is described as follows: Before mixing, the solid and liquid components are equilibrated for at least 10 hours in an incubator at 23° C. 20.0 g of the solid component is placed into a polypropylene beaker followed by 10.0 ml (9.40 grams) of a liquid component comprising methyl methacrylate (MMA) monomer containing 60 ppm of hydroquinone (HQ) inhibitor and 1% w/w with respect to MMA of N,N-dimethyl-para-toluidine (DMPT) accelerator. Hand mixing is then carried out at 23° C. for 30 seconds using a metal spatula, whereupon the material is covered and left to stand. Periodically, the material is assessed for initial mix consistency and dough time determined. For preparing specimens for mechanical testing, doughed material is packed into moulds preconditioned at 23° C. and allowed to harden. The amount of barium sulphate in the total mixture is 20.4% w/w. The flexural strength of the resultant material is 77.3 MPa.

Comparative Example 1

Example 1 is repeated except that the acrylic polymer beads containing encapsulated and/or adsorbed barium sulphate are totally replaced with unfilled poly(methyl methacrylate) (PMMA) beads and the barium sulphate is added as a separate powder ingredient. Additionally, no spray dried emulsion polymer powder is added.

Thus, 14.0 grams of PMMA bead polymer with residual BPO 2.94% w/w and mean particle size of 39 microns were blended with 6.0 grams of barium sulphate (from Sachtleben Chemie GmbH) according to the powder blending method of example 1 to form a solid component. The preparation of a hardenable composition is described as follows: Before mixing, the solid and liquid components are equilibrated for at least 10 hours in an incubator at 23° C. 20.0 g of the solid component is placed into a polypropylene beaker followed by 10.0 ml (9.40 grams) of a liquid component comprising methyl methacrylate (MMA) monomer containing 60 ppm of hydroquinone (HQ) inhibitor and 1% w/w with respect to MMA of N,N-dimethyl-para-toluidine (DMPT) accelerator. Hand mixing is then carried out at 23° C. for 30 seconds using a metal spatula, whereupon the material is covered and left to stand. Periodically, the material is assessed for initial mix consistency and dough time determined. For preparing specimens for mechanical testing, doughed material is packed into moulds preconditioned at 23° C. and allowed to harden. The amount of barium sulphate in the total mixture is 20.4% w/w. The flexural strength of the resultant material is 50.5 MPa.

Comparative Example 2

The acrylic polymer beads containing encapsulated and/or adsorbed X-ray opacifying filler of preparative example 3 were used as the only powder ingredient of the solid component (no spray dried emulsion polymer powder or unfilled acrylic polymer bead is present).

The preparation of a hardenable composition is described as follows: Before mixing, the solid and liquid components are equilibrated for at least 10 hours in an incubator at 23° C. 20.0 g of the solid component is placed into a polypropylene beaker followed by 10.0 ml (9.40 grams) of a liquid component comprising methyl methacrylate (MMA) monomer containing 60 ppm of hydroquinone (HQ) inhibitor and 1% w/w with respect to MMA of N,N-dimethyl-para-toluidine (DMPT) accelerator. Hand mixing is then carried out at 23° C. for 30 seconds using a metal spatula, whereupon the material is covered and left to stand. Periodically, the material is assessed for initial mix consistency and dough time determined. For preparing specimens for mechanical testing, doughed material is packed into moulds preconditioned at 23° C. and allowed to harden. The amount of barium sulphate in the total mixture is 20.4% w/w. The flexural strength of the resultant material is 71.6 MPa.

Table 1 compares the flexural strength results for the final materials prepared in the examples with the comparative examples.

TABLE 1

| | Characteristics of solid component[1] | Amount of barium sulphate in final cement (% w/w) | Flexural strength (MPa) |
|---|---|---|---|
| Example 1 | Mixture consisting of beads containing encapsulated barium sulphate, unfilled beads and spray dried emulsion powder | 20.4 | 75.0 |
| Example 2 | Mixture consisting of beads containing encapsulated barium sulphate and spray dried emulsion powder | 20.4 | 77.3 |
| Comparative example 1 | Mixture consisting of unfilled beads and barium sulphate powder | 20.4 | 50.6 |
| Comparative example 2 | Beads containing encapsulated barium sulphate | 20.4 | 71.6 |

Notes:
[1]'Beads containing encapsulated barium sulphate' means acrylic polymer beads containing encapsulated and/or adsorbed barium sulphate.
2. 'Unfilled beads' means acrylic polymer beads that do not contain any radiopacifying filler.
3. 'Spray dried emulsion powder' means coalesced emulsion polymerized microparticles of PMMA.

Comparison of examples 1 and 2 with comparative example 1 shows how the mechanical properties (as measured by flexural strength) of the final hardenable compositions are enhanced by the use of acrylic polymer beads containing encapsulated and/or adsorbed barium sulphate to make the final hardenable composition instead of using barium sulphate as a separate powder ingredient.

Further, comparison of example 2 with comparative example 2 (which both involve use of acrylic polymer beads containing encapsulated and/or adsorbed barium sulphate) demonstrates how the inclusion of spray dried emulsion powder in example 2 leads to an enhancement of flexural strength compared to comparative example 2, and a surprising improvement in the mechanical properties of the overall material.

Example 3

This example demonstrates that the spray dried powder of preparative example 1 consists of a network of coalesced emulsion polymerized microparticles which is microporous. A sample of the spray dried powder of preparative example 1 was examined by scanning electron microscopy (SEM) to show the morphology of the material. The method involves sprinkling a sample of acrylic polymer particles onto a conducting self-adhesive carbon tab on a standard aluminium SEM stub. The sample is coated with a thin layer of metal (Pt) by vacuum metallization to avoid charging in the SEM instrument. SEM images were taken using a Hitachi S4500 Field Emission SEM using accelerating voltage of 3 kV and working distance of 20 mm. Imaging was carried out on several particles and representative images obtained at different magnifications.

Brunauer-Emmett-Teller (BET) surface area analysis and Barrett-Joyner-Halenda (BJH) pore volume analysis was also carried out on the powder using a Micromeritics Tristar II 3020 instrument operating at room temperature and using nitrogen as the absorptive gas.

A poly(methyl methacrylate) PMMA bead polymer prepared by suspension polymerization was studied as an example of a material that is not considered to be microporous. This was Colacryl® B866, obtained from Lucite International Speciality Polymers & Resins Limited (mean particle size 39 microns and reduced viscosity 2.4 dl/g).

FIG. 1 shows the SEM image of the spray dried powder of preparative example 1 and demonstrates that it consists of a network of coalesced emulsion polymerized microparticles. It also shows that the material is microporous in nature, consisting of pores of 0.01-0.2 microns (10-200 nm) in diameter.

FIG. 2 shows the SEM image of Colacryl® B866 PMMA bead polymer at the same magnification. In contrast to FIG. 1, this image shows that the PMMA bead polymer is not microporous.

Table 2 shows the results of BET surface area and BJH pore volume analysis of the two materials. It can be seen that the spray dried powder of preparative example 1 has much higher surface area and pore volume than the PMMA bead polymer, again reinforcing that fact that the network of coalesced emulsion polymerized microparticles is microporous.

TABLE 2

Results of BET and BJH analysis of the spray dried powder of preparative example 1 and a typical PMMA bead polymer

| | | Colacryl® B866 bead polymer (no degassing of sample) | Colacryl® B866 bead polymer (room temperature degassing of sample) | Spray dried powder of preparative example 1 (no degassing of sample) | Spray dried powder of preparative example 1 (room temperature degassing of sample) |
|---|---|---|---|---|---|
| Surface Area | BET Surface Area: m²/g | 0.9968 | 1.4586 | 22.2453 | 22.1307 |
| | BJH Adsorption cumulative surface area of pores between 2.0000 nm and 500.0000 nm diameter: m²/g | 0.420 | 0.863 | 16.776 | 17.406 |
| Pore Volume | Single point adsorption total pore volume of pores (cm³/g × 10³) | 0.915 | 1.642 | 39.091 | 39.023 |

TABLE 2-continued

Results of BET and BJH analysis of the spray dried powder of preparative example 1 and a typical PMMA bead polymer

|  | Colacryl ® B866 bead polymer (no degassing of sample) | Colacryl ® B866 bead polymer (room temperature degassing of sample) | Spray dried powder of preparative example 1 (no degassing of sample) | Spray dried powder of preparative example 1 (room temperature degassing of sample) |
|---|---|---|---|---|
| BJH Adsorption cumulative volume of pores (cm$^3$/g × 10$^3$) between 2.0000 nm and 500.0000 nm diameter: | 0.729 | 1.496 | 133.932 | 135.282 |
| BJH Desorption cumulative volume of pores (cm$^3$/g × 10$^3$) between 2.0000 nm and 500.0000 nm diameter: | 0.893 | 1.919 | 138.564 | 139.677 |

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A hardenable multi-part acrylic composition comprising
   a solid first part and a storage stable liquid second part and optionally, further solid and/or liquid parts, the parts adapted to form a cement which hardens to a solid mass upon mixing of the parts together, the composition further including:
   an acrylic monomer component in the second part,
   an initiator component,
   a first sub-population of acrylic polymer particles in the first and/or further parts,
   a second sub-population of acrylic polymer particles in the first and/or further parts and optionally, one or more further sub-population(s) of acrylic polymer particles, and
   a radiopacifying filler, wherein:
   the initiator component is present in an amount effective to polymerize the acrylic monomer component upon mixing and/or activating the parts together such that at least some of the radiopacifying filler is encapsulated within and/or adsorbed on the first sub-population of acrylic polymer particles;
   the second sub-population of acrylic polymer particles has a lower average particle size than the first sub-population; and
   the first sub-population is acrylic bead polymer particles produced by suspension polymerization.

2. The hardenable multi-part acrylic composition according to claim 1, wherein the first sub-population of acrylic polymer particles and/or the second sub-population of acrylic polymer particles are in the first part.

3. The hardenable multi-part acrylic composition according to claim 1, wherein between 20 and 100% w/w of the radiopacifying filler in the composition is encapsulated within and/or adsorbed on acrylic polymer particles of the first and/or second sub-population(s) of acrylic polymer particles.

4. The hardenable multi-part acrylic composition according to claim 1, wherein the level of radiopacifying filler in the hardenable multi-part composition is between 1 and 50% w/w.

5. The hardenable multi-part acrylic composition according to claim 1, wherein lower average particle size for the second sub-population of acrylic polymer particles ranges between 0.01-30 µm.

6. The hardenable multi-part acrylic composition according to claim 1, wherein the second sub-population of acrylic polymer particles comprises less than 5% w/w of radiopacifying filler.

7. The hardenable multi-part acrylic composition according to claim 1, wherein average particle size of the first and/or second sub-populations of acrylic polymer particles having encapsulated and/or adsorbed radiopacifying filler ranges from 10 µm to 1000 µm.

8. The hardenable multi-part acrylic composition according to claim 1, wherein the radiopacifying filler comprises zirconium dioxide, strontium carbonate, powdered tantalum, powdered tungsten, barium sulphate, and mixtures thereof.

9. The hardenable multi-part acrylic composition according to claim 1, wherein the hardenable multi-part acrylic composition is adapted for use in the treatment of humans, animals, or bone.

10. A method of producing an acrylic cement from a multi-part acrylic composition comprising:
(i) mixing the multi-part acrylic composition, the multi-part acrylic composition having a solid first part and a storage stable liquid second part and optionally, further solid and/or liquid parts, and further including:
an acrylic monomer component in the second part,
an initiator component,
a first sub-population of acrylic polymer particles in the first and/or further parts,
a second sub-population of acrylic polymer particles in the first and/or further parts and optionally, one or more further sub-population(s) of acrylic polymer particles, and
a radiopacifying filler; and
(ii) forming an acrylic cement from the mixed multi-part acrylic composition of step (i);
wherein:
the initiator component is present in an amount effective to polymerize the acrylic monomer component upon being mixed such that at least some of the radiopacifying filler is encapsulated within and/or adsorbed on the first sub-population of acrylic polymer particles;
the second sub-population of acrylic polymer particles has a lower average particle size than the first sub-population; and
the first sub-population is acrylic bead polymer particles produced by suspension polymerization.

11. A method of producing a hardenable multi-part acrylic composition according to claim 1 comprising:
a) producing an acrylic polymer composition first part and a storage stable second part according to claim 1;
b) wherein step a) comprises the step of polymerizing an acrylic monomer composition to form a sub-population of acrylic polymer particles wherein the polymerization is carried out in the presence of a radiopacifying filler to encapsulate the radiopacifying filler in acrylic polymer particles.

12. A hardenable multi-part acrylic composition comprising
a solid first part and a storage stable liquid second part and optionally, a third or further solid or liquid parts, the parts being operable to form a cement which hardens to a solid mass upon mixing of the parts together, the composition further including:
an acrylic monomer component in the second part,
an initiator component,
a first sub-population of acrylic polymer beads in the first and/or a further part, and
a radiopacifying filler, a second sub-population of acrylic emulsion polymerized microparticles in the first and/or a further part, wherein:
the initiator component is present in an amount effective to polymerize the acrylic monomer component upon being mixed and/or activated such that at least some of the radiopacifying filler is encapsulated within and/or adsorbed on the first sub-population of acrylic polymer beads produced by suspension polymerization.

13. The hardenable multi-part acrylic composition according to claim 12, wherein the emulsion polymerized microparticles are in the form of a network of coalesced emulsion polymerized microparticles.

14. The hardenable multi-part acrylic composition according to claim 13, wherein the network of coalesced emulsion polymerized particles is a porous larger coalesced particle having a large surface area resulting from voids in said particles, and wherein the larger coalesced particles have an average surface area of between 1 and 100 m$^2$/g.

15. The hardenable multi-part acrylic composition according to claim 14, wherein the larger coalesced particles have an average total pore volume of between 0.005 and 0.5 cm$^3$/g.

16. The hardenable multi-part acrylic composition according to claim 12, wherein a total amount of acrylic monomer in the hardenable composition is 10-70% w/w.

17. The hardenable multi-part acrylic composition according to claim 12, wherein at least 90% w/w of the total radiopacifying filler in the composition is present in the acrylic polymer composition first part.

18. The hardenable multi-part acrylic composition according to claim 12, wherein all or substantially all of the acrylic monomer component and the radiopacifying filler are located in separate parts of the composition so that the radiopacifying filler is not substantially present in the polymer matrix of the final hardened material.

19. The hardenable multi-part acrylic composition according to claim 12, wherein at least 90% w/w of the total first or further sub-population acrylic polymer particles with encapsulated and/or adsorbed radiopacifying filler in the composition are present in the acrylic polymer composition first part.

20. The hardenable multi-part acrylic composition according to claim 12, wherein at least 90% w/w of the total second or further sub-population acrylic polymer particles with lower average particle size in the composition are present in the acrylic polymer composition first part.

21. The hardenable multi-part acrylic composition according to claim 12, wherein at least 90% w/w of the total emulsion polymerized microparticles present in the composition whether in the second or further sub-populations are present in the acrylic polymer composition first part.

22. The hardenable multi-part acrylic composition according to claim 12, wherein the multi-part composition is a bone cement composition or dental composition.

23. The hardenable multi-part acrylic composition according to claim 1, wherein the lower average particle size subpopulation(s) are emulsion polymerized microparticles.

24. The hardenable multi-part acrylic composition according to claim 23, wherein when emulsion polymerized microparticles, the Z-average particle size of the lower average particle size sub-population(s) whether the second or further sub-population(s) is preferably in the range 0.01 to 2 µm or when bead particles, the mean particle size of the lower average particle size sub-population(s) whether the second or further sub-population(s), is preferably, in the range 1-30 µm.

25. The hardenable multi-part acrylic composition according to claim 12, wherein at least 90% w/w of the total acrylic polymer bead with encapsulated and/or adsorbed radiopacifying filler in the composition whether in the first or further sub-populations is present in the acrylic polymer composition first part.

26. The hardenable multi-part acrylic composition according to claim 1, wherein at least 90% w/w of the total acrylic polymer bead with encapsulated and/or adsorbed radiopacifying filler in the composition whether in the first or further sub-populations is present in the acrylic polymer composition first part.

27. The hardenable multi-part acrylic composition according to claim 1, wherein a total amount of acrylic monomer in the hardenable composition is 10-70% w/w.

28. The hardenable multi-part acrylic composition according to claim 1, wherein at least 90% w/w of the total radiopacifying filler in the composition is present in the acrylic polymer composition first part.

29. The hardenable multi-part acrylic composition according to claim 1, wherein at least some of the radiopacifying filler remains encapsulated within and/or adsorbed on the first sub-population of acrylic bead polymer particles after polymerization with said monomer and initiator.

30. The hardenable multi-part acrylic composition according to claim 1, wherein at least 90% w/w of the total first or further sub-population acrylic polymer particles with encapsulated and/or adsorbed radiopacifying filler in the composition are present in the acrylic polymer composition first part.

31. The hardenable multi-part acrylic composition according to claim 1, wherein at least 90% w/w of the total second or further sub-population acrylic polymer particles with lower average particle size in the composition are present in the acrylic polymer composition first part.

32. The hardenable multi-part acrylic composition according to claim 1, wherein the multi-part composition is a bone cement composition or dental composition.

* * * * *